US010214396B2

(12) United States Patent
Mupende et al.

(10) Patent No.: US 10,214,396 B2
(45) Date of Patent: Feb. 26, 2019

(54) DEVICE FOR DETERMINING THE REPLACEMENT STATE OR WEAR OF A ROPE DURING USE IN LIFTING GEAR

(71) Applicant: LIEBHERR-COMPONENTS BIBERACH GMBH, Biberach an der Riß (DE)

(72) Inventors: Ilaka Mupende, Neu-Ulm (DE); Horst Zerza, Biberach an der Riß (DE)

(73) Assignee: Liebherr-Components Biberach GMBH, Biberach an der Riss (DE)

( * ) Notice: Subject to any disclaimer, the term of this patent is extended or adjusted under 35 U.S.C. 154(b) by 192 days.

(21) Appl. No.: 15/272,291

(22) Filed: Sep. 21, 2016

(65) Prior Publication Data

US 2017/0066631 A1    Mar. 9, 2017

Related U.S. Application Data

(63) Continuation of application No. PCT/EP2015/000606, filed on Mar. 19, 2015.

(30) Foreign Application Priority Data

Mar. 21, 2014    (DE) .................... 20 2014 002 552 U (51) Int. Cl.
*B66B 7/12*    (2006.01)
*B66B 5/00*    (2006.01)
(Continued)

(52) U.S. Cl.
CPC ............. *B66C 13/16* (2013.01); *B66C 15/00* (2013.01); *B66D 1/54* (2013.01); *D07B 1/145* (2013.01);
(Continued)

(58) Field of Classification Search
CPC ..... D07B 1/145; B66B 7/1215; B66B 7/1223; B66B 7/123; B66B 7/1238; B66C 13/16; B66C 15/06
See application file for complete search history.

(56) References Cited

U.S. PATENT DOCUMENTS

| 4,992,778 A | 2/1991 | McKeen et al. |
| 8,073,653 B2 | 12/2011 | Suzuki et al. |

(Continued)

FOREIGN PATENT DOCUMENTS

| DE | 102004007504 | 11/2009 |
| DE | 102011018535 | 10/2012 |

(Continued)

OTHER PUBLICATIONS

United States, Newman, D. "Naval Ships' Technical Manual—Chapter 613: Wire and Fiber Rope and Rigging", Naval Sea Systems Command, Digital Media Publishing, Aug. 30, 1999.*

*Primary Examiner* — Lisa Caputo
*Assistant Examiner* — Herbert K Roberts
(74) *Attorney, Agent, or Firm* — Levine Bagade Han LLP (57) ABSTRACT

The present invention generally relates to lifting gears such as cranes which use ropes such as high-strength fiber ropes. The invention in particular relates to a device for determining the discard state of such rope in use on such lifting gears, comprising a detection device for detecting at least one rope utilization parameter influencing the discard state and an evaluation unit for evaluating the rope utilization parameter and for providing a discard signal in dependence on the rope utilization parameter evaluation. According to the invention the detection unit has at least one detecting means for detecting environmental influences on the rope, which can be evaluated by evaluation devices to recognize the discard state.

13 Claims, 4 Drawing Sheets

(51) Int. Cl.
  *B66B 5/02*     (2006.01)
  *B66C 13/16*    (2006.01)
  *D07B 1/14*     (2006.01)
  *B66C 15/00*    (2006.01)
  *B66D 1/54*     (2006.01)
  *G01N 17/00*    (2006.01)
  *B66C 23/16*    (2006.01)
  *B66C 23/42*    (2006.01)
  *B66C 23/52*    (2006.01)

(52) U.S. Cl.
  CPC ............ *G01N 17/008* (2013.01); *B66C 23/16* (2013.01); *B66C 23/42* (2013.01); *B66C 23/52* (2013.01)

(56) References Cited

U.S. PATENT DOCUMENTS

2003/0011483 A1*   1/2003   Lamb .................... B66B 7/1223
                                                    340/664
2011/0259677 A1*  10/2011   Dudde ................... B66B 7/062
                                                    187/411

FOREIGN PATENT DOCUMENTS

| EP | 0845672 | 6/1998 | |
| EP | 1357073 | 10/2003 | |
| EP | 2037228 | 3/2009 | |
| WO | WO 2012/100938 | 8/2012 | |
| WO | WO 2012100938 A1 * | 8/2012 | ............ B66C 13/16 |
| WO | WO 2014/006271 | 1/2014 | |
| WO | WO 2014006271 A1 * | 1/2014 | ............ B66B 3/002 |

* cited by examiner

Fig. 1

Fig. 3

DEVICE FOR DETERMINING THE REPLACEMENT STATE OR WEAR OF A ROPE DURING USE IN LIFTING GEAR

CROSS-REFERENCE TO RELATED APPLICATION

The present application is a continuation of International Application No. PCT/EP2015/000606, filed Mar. 19, 2015, which claims priority to German Utility Model Application No. 20 2014 002 552.5, filed Mar. 21, 2014, both of which are incorporated by reference herein in their entireties.

BACKGROUND

1) Technical Field

The present invention generally relates to lifting gears such as cranes which use ropes such as high-strength fiber ropes. The invention in particular relates to a device for determining the discard state of such rope in use on such lifting gears, comprising a detection device for detecting at least one rope utilization parameter influencing the rope discard and an evaluation unit for evaluating the rope utilization parameter and for providing a discard signal in dependence on the rope utilization parameter evaluation.

2) Description of the Related Art

In recent times attempts are made in cranes to use high-strength fiber ropes made of synthetic fibers such as for example aramide fibers (HMPA), aramide/carbon fiber mixtures, high-modulus polyethylene fibers (HMPE) or poly(p-phenylene-2,6-benzobisoxazole) fibers (PBO) instead of the proven steel ropes that have been used for many years. The advantage of such high-strength fiber ropes resides in their low weight. With the same rope diameters and the same or higher tensile strengths, such high-strength fiber ropes are distinctly lighter in weight than corresponding steel ropes. In particular in high cranes with correspondingly large rope lengths this results in a greater weight saving, which feeds into the dead load of the crane and leads to correspondingly higher payloads with otherwise unchanged construction of the crane.

A disadvantageous property of such high-strength fiber ropes however is their breakage behavior or their failure without distinct, longer advance notice. While in steel ropes the wear is readily apparent and a failure is announced quite some time before, for example by the breakage of individual steel wires and by corresponding splicing, which easily is noted, high-strength fiber ropes hardly show any signs of excessive wear, which would easily be perceptible with the eye and would become apparent quite some time before the actual failure. In so far, there is a need for intelligent monitoring measures, in order to recognize the discard state of high-strength fiber ropes in good time.

From DE 199 56 265 B4 a device for monitoring the operation of hoisting winches on cranes is known, which determines the rope force of the hoisting rope and the lever arm of the hoisting rope on the rope winch and therefrom determines the load cycles acting on the rope winch, which are stored in a load spectrum counter. This load spectrum counter is integrated into the hoisting winch, in order to traceably preserve the history of the hoisting winch during removal and re-installation of the same. From EP 0 749 934 A2 there is furthermore known a load spectrum counter which determines the occurring load changes, for each load change determines the rope force applied to the hoisting winch, therefrom calculates the load spectrum and by including the so-called "Wöhler" curves calculates and indicates the remaining service life of the hoisting winch.

Such monitoring measures of the hoisting winch, however, cannot really reliably indicate the remaining service life or the discard state of a high-strength fiber rope, as the high-strength fiber ropes are subject to various loads and impairments influencing wear, which are independent of the loads acting on the winch, e.g. the deflection and bending loads of deflection pulleys, external shocks and blows to the rope, surface impurities of components in contact with the rope, etc. On the other hand, rigid specifications of the lifetime of high-strength fiber ropes hardly are compatible with each other in terms of the economic utilization of the actual lifetime and the necessary safety compliance, as in dependence on the conditions of use and the external influences on the high-strength fiber rope its service life and wear can fluctuate greatly.

From WO 2012/100938 A1 it furthermore is known to monitor several rope parameters of a high-strength fiber rope, which when approaching the discard state show characteristic changes. Even if a rope parameter shows no or no significant or no sufficiently strong change, the discard state can be recognized by monitoring further rope parameters, in particular when several parameters show changes. The detection unit of the device for recognizing the discard state comprises several, differently formed detection means for the magnetic, mechanical, optical and electronic detection of a plurality of different rope parameters, which individually or in combination with each other can be evaluated by the evaluation unit for recognizing the discard state. Despite the evaluation of several rope parameters, however, the problem remains that the discard state not always actually is given with the same changes of rope parameters or there is no rigid connection between individual changes of rope parameters and the discard state. Depending on the individual case, a change in the transverse compressive rigidity or a number of bending cycles can have a different meaning for the discard state.

Proceeding therefrom, it is the object underlying the present invention to indicate an improved device for determining the discard state of high-strength fiber ropes, which avoids disadvantages of the prior art and develops the latter in an advantageous way. Preferably a reliable, precise determination of the discard state should be achieved, which economically makes use of the remaining service life of the fiber rope without putting safety at risk and for this purpose can do with simple detection devices operating reliably also under severe conditions of use for construction machines.

SUMMARY

According to the invention, this object is solved by a device according to claim 1. Preferred aspects of the invention are subject-matter of the dependent claims.

According to an advantageous aspect of the present invention it hence is proposed to also detect environmental influences and/or weather data, to which the rope is exposed when the rope is present on the crane, when determining the discard state, wherein crane operating times and/or downtimes can be taken into account here. While so far one has set on being able to determine the discard state with reference to measurable rope parameters like changing twisting stiffness or bending strength of the rope or optically visible damages such as splicing strands, environmental influences and weather data influencing aging were neglected. Detecting and considering the same, however, provides for a more precise determination of the discard state of a rope, in particular when it is a high-strength fiber rope. According to the invention the detection device has at least one detection means for detecting environmental influences on the rope, which can be evaluated h evaluating devices for recognizing the discard state.

Various environmental influences can be relevant and in so far be detected. For example, particles such as dust, sand or soot depositing on the rope and/or the rope drum can lead to an increased abrasion stress on the rope surface and thereby accelerate the discard state. In accordance with a development of the invention the aforementioned detection means can include a particle detector for detecting the dirt particles present in the ambient air. In dependence on the dirt particle quantity and/or dirt particle quality detected over time, the evaluation device then can determine the discard state of the rope.

On the one hand, the acceleration of the discard state can be inferred from the sheer dirt particle quantity, for example such that at higher particle quantities and/or particle quantities occurring over an extended period the discard state occurs more quickly than at low and/or only briefly occurring particle quantities. Alternatively or in addition to the particle quantity the particle quality or the particle type also can be used to infer the discard state, for example such that harder and/or more sharp-edged and/or more pointed particles bring about the discard state rather than softer and/or rounder particles. For example, sand grains can mechanically impair the rope more strongly than soot particles. The size of the particles detected in the air also can be taken into account in the evaluation, for example such that on the one hand very small particles, whose diameter e.g. lies below a certain threshold value, can impair the discard state more strongly than slightly larger particles, as the very small particles can enter into pores or rope spaces and can wear up the rope front inside. On the other hand, very large particles e.g. in the format of large sand grains in turn can impair the rope more strongly on its surface than medium-sized grains.

Alternatively or in addition to such particle detector the detection means also can comprise a chemical detector which detects certain chemicals that are present in the air in gaseous form or act on the rope in the form of fluids, e.g. strongly acid moisture whose pH value can be detected, or sulfur compounds which can occur in the vicinity of chemical plants, or other chemicals reacting with the rope material or acting thereon. The above-mentioned chemical detector can detect the quantity and/or concentration of the respective chemical and/or determine the respective type of chemical. In dependence on the detected concentration and/or quantity and/or quality the evaluation device then can assess the influence on the discard state, which can be effected e.g. by the fact that the discard state is lowered by a certain percentage as compared to a rope utilized without influence of chemicals.

In accordance with a development of the invention the detection device also can comprise a lubricant detector for detecting lubricants such as oil and grease acting on the rope. When using steel ropes, a sufficient greasing can be monitored or a lack of greasing of the rope can be taken into account, in order to determine the discard state more early. Conversely, in high-strength fiber ropes the discard state also can be shortened or be detected earlier, when lubricants chemically reacting, with the fiber rope, such as certain oils, are in contact with the rope or are found on the rope.

Furthermore, the detection device also can detect bentonite or other substances present on construction sites, such as e.g. lime dust or the like, in order to assess the discard state in dependence on the detected quantity and/or quality.

Alternatively or in addition to the aforementioned environmental influences the aforementioned detection device according to a further aspect of the present invention also can include a weather station for detecting weather data to which the crane or the rope provided thereon is exposed and in dependence on which the evaluation device determines the discard state. Said weather station can detect various climatic situations which can influence the service life of the rope, for example the temperature and/or the UV radiation and/or the amount of precipitation and/or the precipitation profile and/or the air humidity and/or water and/or salt water and/or snow and/or ice.

The evaluation device can be formed such that it processes one or more of the aforementioned rope utilization parameters and takes the same into account in the determination of the discard state. For example, the discard state can be detected earlier when the rope frequently is exposed to very low and/or very high temperatures and/or is utilized, at very low and/or very high temperatures, i.e. is exposed to loads and subjected to bending cycles. Alternatively or in addition, the discard state e.g. can be detected earlier when the crane is used in environments with very high radiation levels, i.e. the rope is exposed to high UV radiation levels which can make high-strength fiber ropes become brittle more early. Alternatively or in addition, high precipitation rates and/or high moisture and/or larger amounts of snow and ice can lead to a shortening of the service life or can lead to an earlier output of the discard signal. Alternatively or in addition it can also be taken into account that salt water at the rope, e.g. at maritime sites of use or also the contact of the rope with water, e.g. in use on offshore platforms or at rivers can shorten the lifetime.

The evaluation device can be formed such that it takes account of said environmental and/or weather influences separately as such. Alternatively or in addition, however, said environmental and/or weather influences also can be linked with other influencing variables and e.g. be taken into account in a manner to increase effectiveness or to decrease effectiveness, e.g. such that very low temperatures during downtimes are not rated or rated only low, while operating times of the crane with very low temperatures are weighted higher, as at very low temperatures the rope then is subjected to bending cycles which impair the rope more strongly than only cold temperatures with the rope at rest.

It can be provided to not rely on a single criterion when determining the discard state, but to circumvent the problem of the only hardly detectable signs of advance notice in that various relevant parameters of the fiber rope or its utilization are monitored and checked for changes and the discard state is determined in the case of a major change of an individual parameter or in the case of several small changes of several parameters. Preferably, the detection device alternatively or in addition to the aforementioned means for determining weather or environmental influences comprises several, differently formed detection means for the magnetic, mechanical, optical and/or electronic detection of several different rope parameters which can be evaluated by the evaluation unit individually or in combination with each other to recognize the discard state. The utilization of various rope parameters such as for example the aforementioned environmental and weather data or mechanical rope parameters such as the transverse compressive rigidity and change in cross-section or alternatively or in addition thereto a rope elongation and magnetic rope properties or other mechanical, optical and/or electronic rope parameters, for the determination of the discard state is based on the consideration that depending on the load and influences on the fiber rope it can be another parameter from case to case, which indicates the rope wear or announces the discard state, or the discard state possibly is not revealed by an actually large change of a single parameter, but by minor changes of several parameters.

In accordance with a development of the invention said evaluating unit is formed such that a discard signal is provided when at least one of the detected rope parameters or their change exceeds or falls below an associated limit value, and when an indirect rope parameter from all detected rope parameters or from a subgroup of the detected rope parameters or its change exceeds or falls below an associated limit value.

In addition to said rope utilization parameters concerning the environmental influences to which the rope is exposed and/or the weather data present during the utilization, the system in particular also can take account of the load spectrum acting on the rope and/or the occurring bending cycles. For determining, the discard state of the fiber rope, in particular the tensile loads acting on the rope and/or the bending cycles acting on the rope can be used as the load spectrum acting on the rope. For this purpose a load spectrum counter can be provided, which as the load spectrum acting on the fiber rope at least detects the tensile load of the rope and the number of bending cycles. The determination and evaluation of said measurement data is possible via corresponding determination means or detection means or sensors whose measurement data are processed and evaluated in the evaluation device. In particular, a load sensor can detect the ongoing load of the rope over the operating time of the rope. For determining the bending cycles a rotational travel sensor on the drum of the rope winch can determine the rope length which is utilized. In the evaluation device the load data and the rope path and bending cycle data can be linked with each other, in order to determine a load spectrum which can be compared with a predetermined, admissible maximum load spectrum. When the number of the maximum admissible load spectrum is reached, the evaluation unit can output a corresponding, discard signal.

In the mathematical determination of the load spectra acting on the rope various analytical approaches can be used in principle. This can be done based on the consideration to infer different degrees of damage on the basis of a mathematical accumulation of damages at various load spectra and to deposit the same in the control system. With a certain specification of load changes, the resulting rope damages thereby can be inferred mathematically, wherein a limit value can be fixed which permits an assessment of the discard state.

For example, in the evaluation of the occurring load spectra a counting method can be employed, wherein for example the amplitude of the occurring loads can be represented over their cumulative frequency. As in the normal case the fiber rope not only is subject to a recurring, equal load with constant amplitude, but to a load variable in its height, the load spectrum occurring in practice for example can be divided or stepped into individual rectangular spectra with constant load each and a number of partial load cycles. For example, according to the known method of the linear damage accumulation, a partial damage now can be calculated for each sub-collective, in that the number of partial load cycles is divided by the maximum tolerable number of load cycles. The resulting partial damages of all sub-collectives can be added up and be used as an indication of the total damage of the fiber rope. In a manner likewise known per se, this approach of the linear damage accumulation also can be modified in various ways, for example to the effect that sub-collectives whose load amplitudes lie below the fatigue limit are not taken into account or only to a limited extent.

In accordance with a development of the invention the aforementioned evaluation unit can be formed for the consideration of several parameters such that not only several rope parameters are detected per se and examined for respective changes or compared with limit values, but dependencies between the several rope parameters also are taken into account. For example, admissible changes and/or admissible limit values for a rope parameter can be shifted or changed when another rope parameter has experienced a predetermined change. In particular more complex fatigues or damages can be detected thereby and the discard state can be recognized. For example, if one proceeds from the tact that a rise in the transverse compressive rigidity is accompanied by a decrease of the rope diameter, the evaluation can lower the limit value for the rope diameter and/or reduce the setpoint range for the admissible rope diameter upon detection of an increased transverse compressive rigidity. When the measurement then detects that the rope diameter falls below the lowered rope diameter limit value and/or falls out of the reduced setpoint range, a discard signal can be generated. In a similar way, further dependencies between the various rope parameters can be taken into account by the evaluation unit alternatively or in addition, for example the aforementioned dependency between rope rigidity and rope elongation, for example such that at a higher flexural rigidity an increasing rope length is expected and taken into account by corresponding limit values.

Alternatively or in addition temporal dependencies of various rope utilization parameters also can be linked with each other and be taken into account in the evaluation, for example such that parts of the load spectrum, which were obtained under unfavorable conditions, for example at very low or very high temperatures and/or at a strong particle load such as e.g. influence of sand, are taken into account more strongly than load spectra occurring, under conditions favorable for the rope. For this purpose, the evaluation device can have a weighting device which weights a rope utilization parameter more strongly when the same occurs under unfavorable conditions and weights the same less strongly when it occurs under favorable conditions or with a favorable other rope parameter. The stronger weighting then can be taken into account by the evaluation device to the effect that this discard state is determined earlier.

In accordance with a development of the invention various other rope parameters can be used in addition to environmental and weather parameters. According to a further aspect of the present invention it is proposed to monitor a change of the transverse compressive rigidity or the rope cross-section and use it as an indicator for the discard state. In particular, the detection device for detecting rope changes can include transverse compressive rigidity and/or cross-section determining means for determining the transverse compressive rigidity or the rope cross-section, wherein the evaluation unit monitors the transverse compressive rigidity or the determined rope cross-section for changes and possibly provides a discard signal.

In endurance tests of high-strength fiber ropes it can be shown that with increasing load and number of bending cycles the transverse compressive rigidity changes in a characteristic way, in particular shows an increase. The degree of the changing transverse compressive rigidity therefore can advantageously be used for fixing the time of the discard state. An increase of the transverse compressive rigidity can be accompanied by a decrease of the rope diameter. The rope can obtain a higher flexural rigidity and/or a permanent, measurable rope elongation can occur. In particular, a dependence of the change of the transverse compressive rigidity on a change of the rope diameter can be detected, wherein in particular an increase of the transverse compressive rigidity in dependence on the decreasing rope diameter can be detected. Alternatively or in addition, a dependence of the change of the rope rigidity on the change of the rope length can be determined, wherein in particular an increase of the rope rigidity in dependence on an increase of the rope length can be determined. The output of the discard signal in principle can be effected solely in dependence on the monitored transverse compressive rigidity or the rope cross-section. By taking account of the dependencies of the various rope parameters on each other, a more precise determination of the discard state however can be effected advantageously.

In accordance with a development of the invention, various other rope parameters can be employed alternatively or in addition to said transverse compressive rigidity or cross-sectional area or form. According to a further aspect of the present invention, a change of an indicator profile embedded in the fiber rope, which consists of a different material than the rope fibers, is monitored here. By means of such indicator profile, which is embedded in the core of the strand or also can be arranged between the fiber strands of the fiber rope, the only hardly detectable change of the fibers or fiber strands of the fiber rope itself can be circumvented, in particular when the indicator profile is chosen such with regard to its formation and/or with regard to its material that the indicator profile shows changes more quickly than the fiber strands of the fiber rope and/or such changes are detectable more easily. Monitoring such indicator profile in the fiber rope also can involve particular advantages only per se without monitoring further parameters.

In accordance with a development of the invention the detection device monitors in which rope portion a change of the rope occurs, which is used for determining the discard state, in order to identify the worn or damaged rope portion and possibly be able to further use the remaining rope, for example in that the damaged part is cut off. In accordance with a development of the invention, rope path and/or position detection means can be associated to the aforementioned detection means, which determine the rope path covered or the position of the rope portion monitored for changes. In particular, said rope path or position detection means can detect a rope winch position, which is given when the rope portion to be examined for changes just is present in the region of the corresponding detection device and actually is monitored for changes. From the above-mentioned rope winch position it can then be back calculated in the evaluation unit which rope portion is damaged or worn.

According to a further advantageous aspect of the present invention an elongation of the fiber rope also can be monitored alternatively or in addition to the above-mentioned monitoring of an embedded indicator profile and be used for determining the discard state. The monitoring of the elongation of the fiber rope proceeds from the consideration that an increasing wear or damage at the fiber rope or the approach to the discard state is accompanied by an elongation of the fiber rope as compared to its original state, so that monitoring of the elongation of the fiber rope can be utilized as an indicator for the discard state. The detection device therefor can include determination means for determining the elongation of the fiber rope, wherein the evaluation unit matches the determined elongation with an admissible maximum elongation. As soon as the elongation exceeds a predetermined degree, the discard state can be indicated.

BRIEF DESCRIPTION OF THE DRAWINGS

The invention will subsequently be explained in detail with reference to a preferred exemplary embodiment and associated drawings. In the drawings.

DETAILED DESCRIPTION

Figure 1:
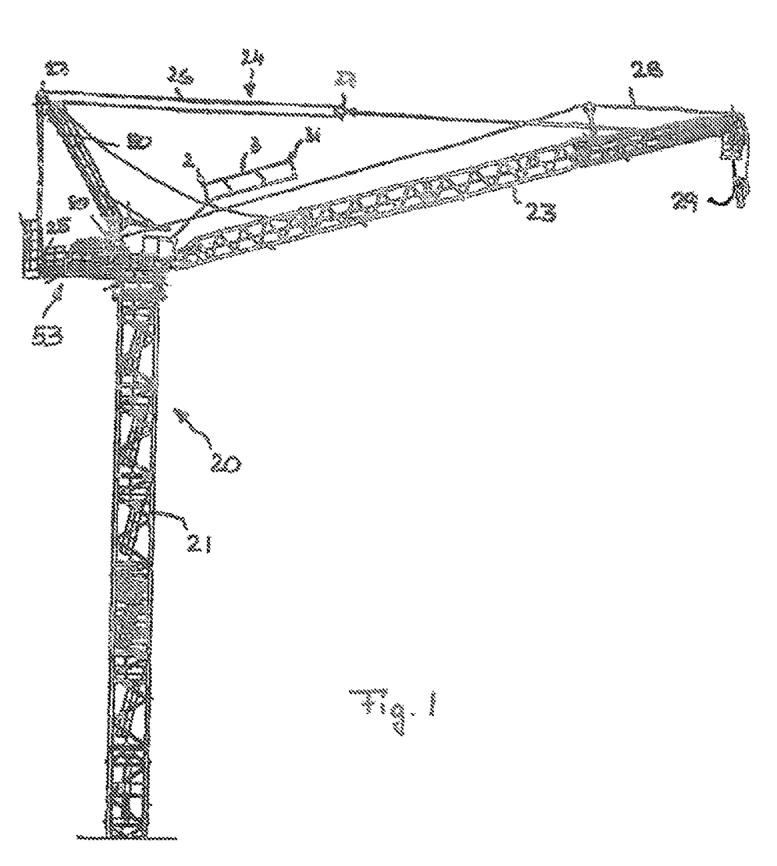
FIG. 1: shows a schematic representation of a lifting gear according to the invention in the form of a tower crane according to an advantageous embodiment of the invention, whose hoisting rope and/or whose guy ropes for the luffing boom can be formed as fiber ropes.

FIG. 1 by way of example for a lifting gear according to an embodiment of the invention shows a crane in the form of a top-slewing tower crane 20, whose tower 21 is mounted on a carriage or a fixed base. In a manner known per se, a boom 23 is luffably articulated to the tower 21 about a horizontal axis and braced via a guy stranding 24. Said guy stranding 24 is variable in its length via a guy rope winch 25, so that the boom 23 can be varied in its pitch angle. For this purpose, a guy rope 26 runs onto said guy rope winch 25. Via deflection pulleys 27 for example at the illustrated guy strut 50 or a tower tip, the guy rope 26, or the guy stranding 24, is guided at an articulation point on the boom 23 in the vicinity of the tip of the boom 23.

Alternatively, the tower crane 20 can of course also be provided with a trolley boom. On the boom 23 a trolley can be movably mounted, which for example can be moved by means of a trolley rope that can be guided over deflection pulleys at the boom tip.

Furthermore, the tower crane comprises a hoisting rope 28 which in the illustrated embodiment according to FIG. 1 can be lowered from the tip of the boom via deflection pulleys at the boom tip and is connected there with a crane hook 29, or can unwind via said movable trolley and deflection pulleys provided there and be connected with the crane hook 29. Said hoisting rope 28 in both cases runs onto a hoisting winch 30, which like the guy rope winch 25 of the embodiment of FIG. 1 is arranged in the region of the ballast frame or another carrier part on the counter-boom 53.

Said hoisting rope 28 and/or the guy rope 26 here can be formed as fiber rope which can consist of synthetic fibers such as e.g. aramide fibers or an aramide/carbon fiber mixture, or can also be formed as steel strand part or as mixed form.

Figure 2:
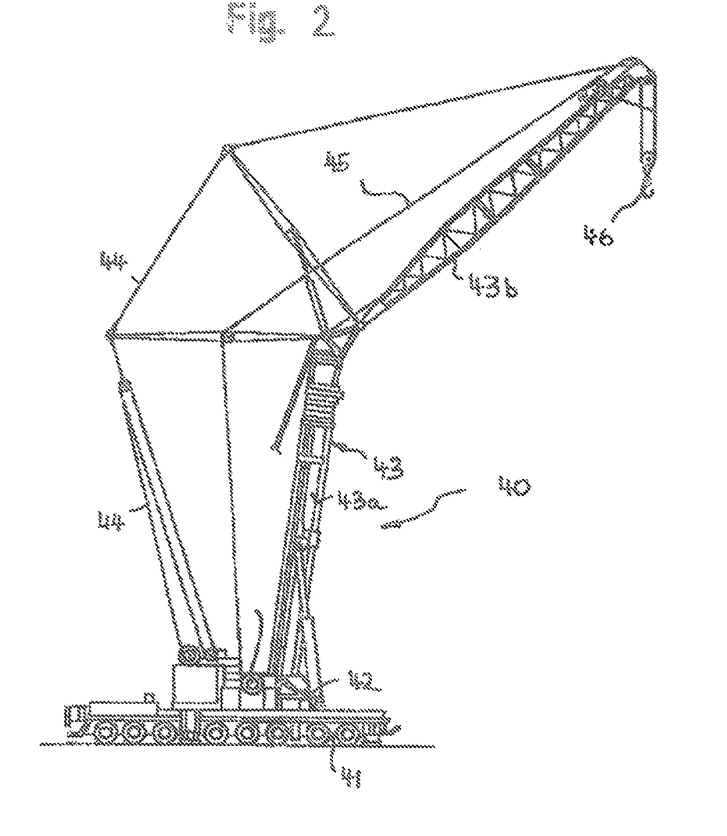
FIG. 2: shows a schematic representation of a telescopic vehicle crane whose hoisting rope is monitored for its discard state.

As shown in FIG. 2, the lifting gear also can be formed as mobile crane or vehicle crane 40, which can comprise an undercarriage 41 formed as truck on which a turntable 42 can rotatably be mounted about an upright axis. On said turntable 42 a crane boom 43 can be arranged, which with said turntable 42 is rotatable about the upright axis and is luffable up and down about a horizontal tufting axis. As shown in FIG. 2, said crane boom 43 can comprise a telescopic boom 43*a* which can be telescoped in and out, wherein on said telescopic boom 43*a* a luffing jib 43*b* can be mounted, which for example can be formed as lattice boom. By means of a guy stranding 44 said crane boom 43 can be braced and the lulling jib 43*b* possibly can also be luffed up and down. A hoisting rope 45 can unwind via the luffing jib 43*b* and be reeved on a crane hook 46 in a manner known per se.

Figure 3:
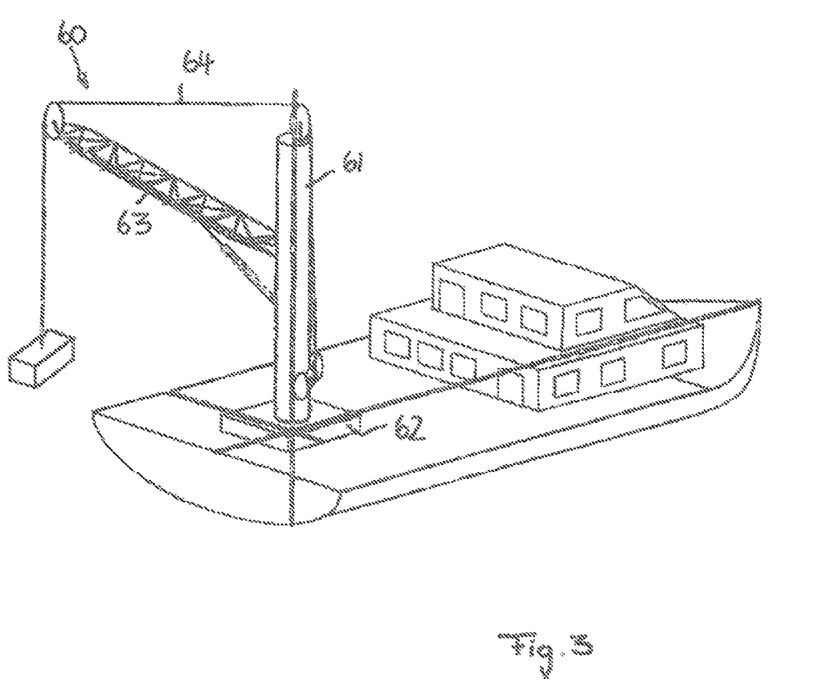
FIG. 3: shows a schematic representation of a harbor crane whose ropes are monitored for their discard state.

As shown in FIG. 3, the lifting gear also can be formed as ship crane 60 or harbor crane, which comprises a portal post 61 that substantially extends upright and is rotatably anchored on an anchorage base 62 about an upright axis. To said portal post 61 a crane boom 63 can luffably be articulated, over whose tip a hoisting rope 64 is unwound.

Said guy and hoisting ropes 44 and 45 as well as 64 of the cranes of FIGS. 2 and 3 likewise can be formed in the above-mentioned way as high-strength fiber rope, but possibly can also be a steel rope.

In the following reference only is made to a rope 1, by which any of the aforementioned guy or hoisting ropes can be meant.

To be able to monitor or detect parameters of said fiber rope relevant for the discard state, a detection device 2 is provided, which can be arranged on the crane and together with an evaluation device 3, which evaluates the detected parameters, can be connected with the electronic crane control unit 31 or be integrated into the same.

Figure 4:
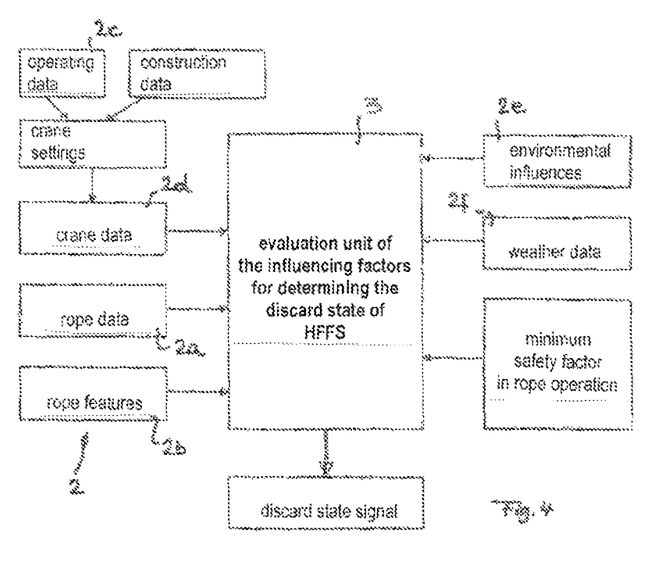
FIG. 4: shows a schematic representation of the device for recognizing the discard state of the rope of one of the lifting gears from the preceding Figures, wherein the evaluation unit and the rope utilization parameters taken into account by the same are shown.

As shown in FIG. 4, the detection device 2 comprises various detection means, in order to on the one hand monitor the rope 1 itself and provide rope data and rope features to the evaluation unit 3. The detection means 2*a* in particular can provide mechanical parameters of the rope 1, e.g. make and material of the rope, minimum rope tension with empty load hook, maximum admissible rope tension, and minimum breaking, force of the rope. Furthermore, said detection means 2*a* can provide the transverse rigidity of the rope and/or the flexural rigidity of the rope and/or the torsional rigidity of the rope, wherein here on the one hand the values of said quantity in the new state of the rope can be provided as stored values and an ongoing monitoring can take place. Said rope parameters such as transverse rigidity, flexural rigidity and torsional rigidity can be monitored and determined by measuring and/or detection means, as is explained for example in the document WO 2012/100 938.

The detection means 2*b* for the provision of the rope features as shown in FIG. 4 for example can provide optical damage features which are detectable e.g. by a camera, and/or operational features which can be determined by data acquisition on the crane. In particular, said detection means 2*b* can provide mechanical damages e.g. in the form of grinding marks on the rope sheath in signal form, or also similar damages, e.g. when the rope sheath is torn up and/or detaches from the rope. Alternatively or in addition cut surfaces and/or pinchings of the rope or similar damaged spots of the rope sheath and/or of the rope strands due to external influence can be indicated and provided. Alternatively or in addition a hump formation can be detected and provided by outputting signals, e.g. by a strong shifting of the rope strands. Alternatively or in addition a strong twisting of the rope sheath and/or twists per length unit can be determined and provided.

Depending on the degree of deterioration as regards said features, the evaluation unit 3 can provide a discard signal.

The detection means 2*b* furthermore can determine operational features by corresponding measuring devices on the crane and provide the same to the evaluation device, such as changes of the rope diameter and/or a rope elongation.

Furthermore, a rope efficiency can be determined, i.e. changes due to aging and the operating time. Alternatively or in addition the rope temperature can be detected, which due to the crane operation and the ambient temperature occurs during the crane operation. For example, when a maximum admissible rope temperature is exceeded, switch-over to adapted partial load operation can be effected to maintain the rope safety. Alternatively or in addition the aging of the rope in particular in the form of a reached lay-up time can be determined, wherein a maximum admissible lay-up time can be assessed in dependence on various influencing factors.

Furthermore, as shown in FIG. 4, various crane data can be supplied to the evaluation device 3, for example construction data and crane settings such as e.g. diameters of rope drums and rope pulleys, rope lengths and rope diameters, the number of reevings, drum dimensions in the form of drum diameter and sheath length, the number of the maximum rope layers on the drum, and the number of the windings, and/or rope velocities maximally provided for the respective rope.

Furthermore operating data also can be provided as crane data, which can be detected during the crane operation by means of corresponding detection means 2*e*, for example the load range occurring in operation and the time of loading, a load measurement based on a rope strand, which for example can be effected by a load sensor, and/or the lifting height or the rope path length depending on the load cycle, wherein here e.g. a measurement can be made by a revolution sensor at the rope drum. Alternatively or in addition the actually realized rope velocity can be measured, e.g. by a correspond me rotational speed sensor at the rope drum.

In particular, said detection device 2 also can include detection means 2*d* for detecting the load spectrum acting on the respective fiber rope 1, wherein here advantageously at least the tensile load acting on the rope and the number of the bending cycles, but advantageously also other parameters influencing the fatigue strength such as multi-layer spooling, environmental influences, temperature, transverse loads and other factors can be detected.

For determining said parameters, said detection means 2*d* comprise corresponding sensors whose signals are evaluated in said evaluation unit 3. In particular, a load measurement sensor can detect the current loading of the rope over the operating time of the rope. Advantageously, a rotational path sensor on the respective winch drum furthermore can measure the rope length which is demanded. In total, a load spectrum for example in the form of a "Wöhler" curve can be determined therefrom, which can be compared with a specified maximum load, spectrum for the fiber rope 1. When the number of the maximum admissible load spectrum, i.e. a particular number of bending cycles under the influence of a particular load and/or particular load peaks, is reached, a warning and/or a specification as to the time in which the rope replacement must be effected, can be performed.

Furthermore, the detection device 2 has detection means 2*e* for detecting environmental influences which act on the ropes 1 provided at the respective crane. Said detection means 2*e* advantageously can likewise be provided at the respective crane.

Possible environmental influences which can influence the service life of the rope and in so far can be detected by the detection means 2*e*, include e.g. dust, sand and/or soot, and/or lubricants such as oils, greases which are in contact with the respective rope or are detectable e.g. in the form of oil mist in the air. Alternatively or in addition to such oils and greases bentonite can also be detected. Alternatively or in addition other chemicals which can influence the service life of the rope can be detected as well. The aforementioned detection means 2e for detecting the aforementioned substances can comprise a particle detector for detecting, the dirt particles present in the ambient air, a lubricant detector or suitable chemical sensors which can be placed at a suitable point on the respective crane.

The influencing factors of the aforementioned environmental influences on the discard state or the service life of the rope can be determined in advance by experiments, so that the detected environmental influences and their quantity, e.g. dust particle quantities and types and sizes can be scaled with the respective influencing factor and be converted by the evaluation device 3 into a corresponding shortening of the service life.

Alternatively or in addition to the aforementioned detection means 2e for environmental influences the detection device 2 furthermore also can comprise weather data detection means 2f, by means of which possible climatic situations, which can influence the service life of the rope, can be detected. Said detection means 2f for example can be arranged at the respective crane or in direct vicinity thereof in the form of a weather station and provide corresponding weather data to the evaluation device 3, as is shown in FIG. 4.

Said detection meat 21 in particular can detect the ambient temperature and/or occurring UV radiation and/or the precipitation profile and/or humidity and/or water and/or salt water and/or snow and/or ice as rope utilization parameters, wherein advantageous y upon detection it is registered whether the corresponding weather data occur during the crane operation or during downtimes.

Influencing factors for the respective weather parameters on the discard state or the service life here can also be determined by means of experiments, for example to find out how much a very low temperature on lifting loads and corresponding bending cycles with loads in a specified weight range have an effect on the service life of the rope. Correspondingly determined influencing factors can be used for scaling the weather data, wherein here a distinction can be made in the above-mentioned way between climatic situations during crane operation and climatic situations during downtimes. By means of said influencing factors, the evaluation device can convert the occurring climatic situations into a corresponding shortening of the service life or an early occurrence of the discard state.

The signal indicating the discard state advantageously can be output by the evaluation device 3 in several stages, for example be indicated at the crane monitor of the crane controller. For example, a first stage can indicate, e.g. in green color, that safety still exists up to a minimum rope safety factor of 2. In a second stage, e.g. yellow, the presence of safety up to at least a rope safety factor of 1.5 can be indicated. In a third stage, it can be indicated e.g. in red that safety only reaches up to the minimum rope safety factor of 1.0. The latter stage or latter signal of the evaluation device 3 for example can be used to reduce the rope tensile force maximally admissible for an even further operating time to a predetermined value, e.g. 50% of the rope tensile force admissible in a new rope. When the rope is not renewed in such remaining time window, load lowering might be effected to almost 0.

We claim:

1. A device to determine a discard state of a rope in use on lifting gears, comprising:
   a rope utilization detector to detect at least one rope utilization parameter influencing the discard state of the rope, and
   an evaluation unit to evaluate the at least one rope utilization parameter and to provide a discard signal based on the evaluation of the rope utilization parameter,
   wherein the rope utilization detector includes at least one detection component to detect the at least one rope utilization parameter, and wherein the rope utilization parameter includes at least one of a weather and a climate-based parameter prevailing at one or more lifting gears and
   wherein the detection component comprises a UV radiation sensor to determine an amount of UV radiation acting on the rope, wherein the UV radiation sensor comprises a radiation dosimeter.

2. The device according to claim 1, wherein the evaluation unit outputs a discard signal when at least one of the rope utilization parameters or changes thereof detected by the rope utilization detector exceeds or falls below an associated limit value, and when an indirect sum parameter derived from all or some of the rope utilization parameters detected by the rope utilization detector, or their changes thereof, exceeds or falls below another associated limit value.

3. A device to determine a discard state of a rope in use on lifting gears, comprising:
   a rope utilization detector to detect at least one rope utilization parameter influencing the discard state of the rope, and
   an evaluation unit to evaluate the at least one rope utilization parameter and to provide a discard signal based on the evaluation of the rope utilization parameter,
   wherein the rope utilization detector includes at least one detection component to detect the at least one rope utilization parameter, and wherein the rope utilization parameter includes at least one of a weather and a climate-based parameter prevailing at one or more lifting gears,
   wherein the detection component comprises at least one of a precipitation sensor and a humidity sensor to determine at least one of a precipitation profile and the humidity in a vicinity of the rope, and
   wherein the humidity sensor includes a salt content detector to determine the salt content in the humidity determined in the vicinity of the rope, wherein the salt content is used by the evaluation unit to evaluate the discard state of the rope.

4. A device to determine a discard state of a rope in use on lifting gears, comprising:
   a rope utilization detector to detect at least one rope utilization parameter influencing the discard state of the rope, and
   an evaluation unit to evaluate the at least one rope utilization parameter and to provide a discard signal based on the evaluation of the rope utilization parameter,
   wherein the rope utilization detector includes at least one detection component to detect the at least one rope utilization parameter, and wherein the rope utilization parameter includes at least one of a weather and a climate-based parameter prevailing at one or more lifting gears, and
   wherein the detection component comprises at least one of a snow sensor and an ice sensor to detect at least one of an amount and duration of snow and ice, wherein and wherein the amount and duration of snow and ice is used by the evaluation unit to evaluate the discard state of the rope.

5. A device to determine a discard state of a rope in use on lifting gears, comprising:
a rope utilization detector to detect at least one rope utilization parameter influencing the discard state of the rope, and
an evaluation unit to evaluate the at least one rope utilization parameter and to provide a discard signal based on the evaluation of the rope utilization parameter,
wherein the rope utilization detector includes at least one detection component to detect the at least one rope utilization parameter, and wherein the rope utilization parameter includes at least one of an environmental and a chemical parameter prevailing at one or more lifting gears, and
wherein the detection component comprises a particle detector to detect at least one of an amount of dirt particles and a type of dirt particles present in the ambient air in the vicinity of the rope over time and the evaluation unit uses at least one of the amount of dirt particles and the type of dirt particles detected by the particle detector over time to evaluate the discard state of the rope.

6. The device according to claim 5, wherein the particle detector detects at least one of dust particles, sand particles, and soot particles.

7. The device according to claim 5, wherein the detection component comprises a lubricant detector to detect lubricants acting on the rope including at least one of oils and greases.

8. The device according to claim 5, wherein the detection component comprises at least one chemical sensor to detect chemicals impairing the rope and the evaluation unit uses at least one of an amount of chemicals detected and a type of chemicals detected over time by the at least one chemical sensor to evaluate the discard state of the rope.

9. A device to determine a discard state of a rope in use on lifting gears, in particular cranes, comprising:
a rope utilization detector to detect at least one rope utilization parameter influencing the discard state of the rope, and
an evaluation unit to evaluate the at least one rope utilization parameter and to provide a discard signal based on the evaluation of the rope utilization parameter,
wherein the rope utilization detector includes at least one detection component to detect the at least one rope utilization parameter, and wherein the rope utilization parameter includes at least one of an environmental and a chemical parameter prevailing at one or more lifting gears, and
wherein the detection component comprises a bentonite sensor to detect bentonite and the evaluation unit uses a quantity of bentonite detected over time to evaluate the discard state of the rope.

10. A method of determining a discard state of a rope used with crane lifting gears, comprising:
detecting, using a rope utilization detector, at least one rope utilization parameter influencing the discard state of the rope, wherein the rope utilization detector comprises at least one detection component to detect the at least one rope utilization parameter, wherein the rope utilization parameter includes at least one of an environmental, a chemical, and a climate-based parameter prevailing at one or more crane lifting gears;
evaluating, using an evaluation unit, the at least one rope utilization parameter detected by the rope utilization detector; and
providing, using the evaluation unit, a discard signal concerning the discard state of the rope when the at least one rope utilization parameter exceeds or falls below an associated limit value,
wherein detecting the rope utilization parameter comprises detecting an amount of UV radiation acting on the rope using a UV radiation sensor.

11. The method of claim 10, wherein detecting the rope utilization parameter comprises detecting at least one of a precipitation profile and a humidity in a vicinity of the rope using at least one of a precipitation sensor and a humidity sensor.

12. A method of determining a discard state of a rope used with crane lifting gears, comprising:
detecting, using a rope utilization detector, at least one rope utilization parameter influencing the discard state of the rope, wherein the rope utilization detector comprises at least one detection component to detect the at least one rope utilization parameter, wherein the rope utilization parameter includes at least one of an environmental, a chemical, and a climate-based parameter prevailing at one or more crane lifting gears;
evaluating, using an evaluation unit, the at least one rope utilization parameter detected by the rope utilization detector; and
providing, using the evaluation unit, a discard signal concerning the discard state of the rope when the at least one rope utilization parameter exceeds or falls below an associated limit value,
wherein detecting the rope utilization parameter comprises detecting, using at least one of a snow sensor and an ice sensor, at least one of an amount of snow or ice and a duration of snow or ice.

13. A method of determining a discard state of a rope used with crane lifting gears, comprising:
detecting, using a rope utilization detector, at least one rope utilization parameter influencing the discard state of the rope, wherein the rope utilization detector comprises at least one detection component to detect the at least one rope utilization parameter, wherein the rope utilization parameter includes at least one of an environmental, a chemical, and a climate-based parameter prevailing at one or more crane lifting gears;
evaluating, using an evaluation unit, the at least one rope utilization parameter detected by the rope utilization detector; and
providing, using the evaluation unit, a discard signal concerning the discard state of the rope when the at least one rope utilization parameter exceeds or falls below an associated limit value,
wherein detecting the rope utilization parameter comprises detecting, using a particle detector, at least one of an amount of dirt, dust, sand, or soot particles and a type of dirt, dust, sand, or soot particles present in the ambient air in the vicinity of the rope over time.

* * * * *